(12) United States Patent
Chen et al.

(10) Patent No.: US 10,990,851 B2
(45) Date of Patent: Apr. 27, 2021

(54) METHOD AND DEVICE FOR PERFORMING TRANSFORMATION-BASED LEARNING ON MEDICAL IMAGE

(71) Applicant: Intervision, Beijing (CN)

(72) Inventors: Kuan Chen, Beijing (CN); Rongguo Zhang, Beijing (CN)

(73) Assignee: Intervision Medical Technology Co., Ltd., Beijing (CN)

( * ) Notice: Subject to any disclaimer, the term of this patent is extended or adjusted under 35 U.S.C. 154(b) by 89 days.

(21) Appl. No.: 16/265,231

(22) Filed: Feb. 1, 2019

(65) Prior Publication Data

US 2019/0180145 A1    Jun. 13, 2019

Related U.S. Application Data

(63) Continuation of application No. PCT/CN2017/087587, filed on Jun. 8, 2017.

(30) Foreign Application Priority Data

Aug. 3, 2016  (CN) .......................... 201610627265.3

(51) Int. Cl.
  *G06K 9/00*    (2006.01)
  *G06K 9/62*    (2006.01)
  *G16Z 99/00*   (2019.01)

(52) U.S. Cl.
  CPC ......... *G06K 9/6257* (2013.01); *G06K 9/6262* (2013.01); *G16Z 99/00* (2019.02); *G06K 2209/05* (2013.01)

(58) Field of Classification Search
  CPC .......... G06N 3/08; G06N 3/088; G06N 20/00; G06N 7/005; G06N 20/10; G16H 30/40;
  (Continued)

(56) References Cited

U.S. PATENT DOCUMENTS 6,418,243 B1 * 7/2002 Skoglund .............. G06T 11/003
                                                345/419
9,008,840 B1 * 4/2015 Ponulak ................... B25J 9/163
                                                700/250
(Continued)

FOREIGN PATENT DOCUMENTS

CN    101188107    5/2008
CN    103488135    1/2014
(Continued)

OTHER PUBLICATIONS

Sawada, "Transfer Learning Method using Multi-Prediction Deep Boltzmann Machines for a small scale dataset" 2015 (Year: 2015).*
(Continued)

*Primary Examiner* — Alex Kok S Liew
(74) *Attorney, Agent, or Firm* — H.C. Park & Associates, PLC

(57) ABSTRACT

A method and device for performing based learning on a medical image includes reading raw data of a medical image, performing transformation processing on the data by analyzing a data attribute, and integrating the same into a data format capable of being received by a model to be trained; selecting a transformation method by comparing parameters of the model to be trained and a trained model, so as to perform parameter transformation and apply transformation-based learning to training of the model to be trained for the medical image; and upon finishing model training, applying a parameter of a trained model to image category analysis. The invention further includes a device for performing transformation-based learning on a medical image, including: a data processing module; a transformation-based learning module; and an application module.

12 Claims, 5 Drawing Sheets

(58) Field of Classification Search
CPC ........ G16H 50/50; G16H 50/70; G16H 30/20;
G16H 40/40; G16H 10/60; G16H 50/20;
G16H 15/00; G16H 40/20; G16Z 99/00;
A61B 5/0013; A61B 5/0022; A61B
5/7267; A61B 6/52; A61B 5/00; A61B
5/7246; A61B 5/11; A61B 2090/364;
A61B 6/469; A61B 6/5247; G06K
2209/05; G06K 9/3233; G06K 9/6255;
G06K 9/4647; G06K 9/6202; G06K
9/6264; G06K 9/6256; G06K 9/6267;
G06K 9/6262; G06K 9/4628; G06K
9/6257; G06K 9/6259; G06T 2207/10116;
G06T 7/73; G06T 7/0012; G06T 7/11;
G06T 7/30; G06T 15/00; G06T 19/20;
G06T 2207/20081; G06T 17/00; G06T
7/246; G06T 2207/10012; G06T 7/70;
G06T 7/0002; G06T 2207/20084; G06T
2207/30096; G06T 2207/10081; G06T
2207/30168; G06T 2207/10088; G06T
11/008; G06T 2200/16; G06T 2200/24;
G06T 2207/10056; G06T 2207/20104;
G06T 7/0014; G06T 7/10; G06T 19/006;
G06T 2207/20016; G06T 2207/20041;
G06T 2207/20152; G06T 2207/20156;
G06T 2207/30024; G06T 5/50; G06T
7/12; A61N 1/3603; G06F 3/015; G06F
11/30; G06F 2111/10; G06F 19/321
USPC ............ 382/128, 129, 131, 132, 154, 284;
600/447
See application file for complete search history.

(56) References Cited

U.S. PATENT DOCUMENTS

| | | | | |
|---|---|---|---|---|
| 9,036,898 | B1* | 5/2015 | Beeler | G06T 19/20 382/154 |
| 9,633,282 | B2* | 4/2017 | Sharma | G06K 9/6256 |
| 10,664,999 | B2* | 5/2020 | Gupta | G06T 3/40 |
| 2006/0064017 | A1* | 3/2006 | Krishnan | G06K 9/6282 600/450 |
| 2006/0161218 | A1* | 7/2006 | Danilov | A61N 1/36014 607/45 |
| 2007/0165920 | A1* | 7/2007 | Gering | A61B 5/055 382/128 |
| 2011/0052026 | A1* | 3/2011 | Liao | G06T 7/73 382/131 |
| 2011/0161056 | A1* | 6/2011 | Mueller | B29C 64/165 703/1 |
| 2013/0177235 | A1* | 7/2013 | Meier | G06T 15/00 382/154 |
| 2013/0178952 | A1* | 7/2013 | Wersborg | B23K 26/032 700/47 |
| 2013/0343642 | A1* | 12/2013 | Kuo | G06K 9/4652 382/159 |
| 2014/0005547 | A1* | 1/2014 | Balasubramanian | A61B 8/467 600/447 |
| 2014/0188768 | A1* | 7/2014 | Bonissone | G06N 20/00 706/12 |
| 2015/0063681 | A1* | 3/2015 | Bhardwaj | G06T 7/194 382/154 |
| 2015/0127155 | A1* | 5/2015 | Passot | B25J 9/161 700/257 |
| 2015/0371420 | A1* | 12/2015 | Yerushalmy | G06T 3/4038 382/284 |
| 2017/0091951 | A1* | 3/2017 | Yoo | G06T 7/11 |
| 2017/0132528 | A1* | 5/2017 | Aslan | G06N 20/00 |
| 2017/0372221 | A1* | 12/2017 | Krishnamurthy | G06N 7/005 |
| 2018/0137941 | A1 | 5/2018 | Chen | |
| 2018/0144214 | A1* | 5/2018 | Hsieh | G06N 3/08 |
| 2018/0144465 | A1* | 5/2018 | Hsieh | G06N 3/08 |
| 2018/0144466 | A1* | 5/2018 | Hsieh | G06T 7/0012 |

FOREIGN PATENT DOCUMENTS

| | | |
|---|---|---|
| CN | 104463965 | 3/2015 |
| CN | 104657596 | 5/2015 |
| CN | 104866727 | 8/2015 |
| CN | 105354986 | 2/2016 |

OTHER PUBLICATIONS

Shin "Deep Convolutional Neural Networks for Computer-Aided Detection: CNN Architectures Dataset Characteristics and Transfer Learning," May 2016, IEEE (Year: 2016).*

International Search Report dated Sep. 13, 2017, issued in International Patent Application No. PCT/CN2017/087587 (with English Translation).

* cited by examiner

METHOD AND DEVICE FOR PERFORMING TRANSFORMATION-BASED LEARNING ON MEDICAL IMAGE

CROSS REFERENCE TO RELATED APPLICATION

This application is a Bypass Continuation of International Patent Application No. PCT/CN2017/087587, filed on Jun. 8, 2017, and claims priority from and the benefit of Chinese Patent Application No. 201610627265.3, filed on Aug. 3, 2016, each which is incorporated by reference for all purposes as if fully set forth herein.

BACKGROUND

Field

Exemplary embodiments of the invention relates generally to the field of medical artificial intelligence and big data processing, more specifically, to a method and device for performing transfer learning on medical images.

Discussion of the Background

With its strong rise, the new artificial intelligence technology having the deep learning framework as its core has achieved considerable development and advancement in various fields. Deep learning is part of machine learning methods based on learning data representations, which is a set of techniques that allows a computer system to automatically discover the representations needed for feature detection or classification from raw data. Breakthroughs are achieved in AlphaGo, automation vehicles, speech recognition and other technologies that people have been expecting for years in a very short time as well. In the foreseeable future, deep learning will also promote the applications of big data analysis and artificial intelligence in medical industry.

However, even with the above breakthroughs, currently deep learning technology is still facing significant problems in the training process:

i) Model training is costly. The best applied deep learning and big data analysis models are very large models having inordinate amounts of data. The amount of data required to train the model resulted in the large size of models, especially in fields like medical imaging. The amount of data required for deep learning increases exponentially when the feature/pattern to be detected are more complex, such as required to recognize medical images, including, e.g., pulmonary nodules from a X-ray image, or even from a computed tomography (CT) image. It usually takes at least one week for a Graphics Processing Unit (GPU) to train such a model to recognize a complex pattern from the beginning, and it takes several weeks or even months for a Central Processing Unit (CPU) to do so. Also, this model training process consumes a lot of time and manpower. It is also difficult for the modeler to achieve rapid iteration as well as research & development of the model.

ii) Training data for some application scenarios are limited; the information contained in the data is not enough to support the training of a large deep learning model, thus seriously limiting the range of application of deep learning model in such application scenarios.

In the medical industry, such as medical imaging, the above two issues result in significant technical problems, e.g., as follows:

1) The dimensions in medical field are more than that of the general application scenario. The diagnosis and treatment data of each patient are complicated. The deep learning and data analysis models are also larger and more complex than the general ones. The training costs are very high. Learning and training for deep learning and big data and machine learning models with traditional methods consume a lot of manpower and material resources, greatly reducing the economic feasibility of the application.

2) Although the overall amount of data in the medical fields such as medical imaging, is large, data sources are distributed over hospitals and other clinical settings; thus there are no unified databases available. The amount of data (such as the number of cases) around a single application scenario, such as lung cancer, for example, is very limited. And the limited variables of data are insufficient to support training and computing large deep learning and big data models, therefore greatly limiting the scenarios in which deep learning and big data technologies could be applied.

Both of the above-mentioned issues greatly limit the development and continued progress of the overall technology of deep learning in the medical industry.

In the training module of general deep learning and big data modeling, sample data are used to optimize and calculate the parameters in the model. Through analysis and calculation of the training module, deep learning and big data model parameters become more and more optimized, which ultimately leads to an optimized model that performs specific functions. Therefore, the optimization process through sample training is crucial in the modeling of big data, machine learning and deep learning.

Modeling in medical industry often requires complex and large deep learning and big data models to learn and train data because of complex scenarios involved. However, the number of samples is often limited in different application scenarios. This brings a lot of pressure to the parameter optimization procedure in the deep learning and big data modeling training module. Usually, the amount of available data is not enough to support the sample needed by the whole model to complete the optimization. In most cases the model is not effective enough after computation, and optimal points are not found in the optimization process.

The above information disclosed in this Background section is only for understanding of the background of the inventive concepts, and, therefore, it may contain information that does not constitute prior art.

SUMMARY

In order to overcome one or more of the deficiencies and drawbacks of the prior art, the invention provides a method and device for performing transfer learning on medical images, which effectively solve one or more of the above optimization problems, and improve the practical ability to use deep learning techniques in the field of medical images.

More specifically, according to the principles and exemplary embodiments of the invention, one or more parameters of a model trained in other application scenarios are loaded into an existing model before the deep learning model or the big data model begins to perform learning and optimization on the training data and before the normal optimization operation of the model is started. Thus, methods and devices constructed according to the principles and exemplary embodiments of the invention help the model to start optimization at an ideal starting point in the parameter space that facilitates the model to find a better optimization point in a shorter time with less training samples, thus greatly lowering the cost and conditions of model training, and allowing the model to be applied in more application scenarios.

For example, one specific embodiment of the invention was used to transfer a data model for analyzing femoral head to analyze and calculate thoracic pulmonary diseases for further improvement and analysis. Without using the parameter transfer features of the invention, when only pulmonary disease images were used for training, the accuracy of the model only reached 65%. On the contrary, after transferring the parameters of the data model for analyzing femoral head to the pulmonary disease model in accordance with the principles of the invention, the accuracy of the training model reached more than 85%, thus reducing the difficulty and cost of modeling and analysis of pulmonary diseases.

According to one embodiment of the invention, a method for performing transfer learning on medical images, including the steps of: reading raw data information related to a first type of medical images, transforming the raw data by analyzing a data attribute of the raw data, and adjusting the raw data into a data format of a model to be trained for a second type of medical images; selecting a parameter transformation method from the group consisting of a complete transfer method, a partial transfer method, a hybrid transfer method, a parameter transformation method, a timing import method, and a customized import method by comparing parameters of the model to be trained with parameters of a model already trained; performing the selected method of parameter transformation, and applying the transfer learning to training of the model for the first type of medical images; and applying the parameters of the model already trained to the analysis for the second type of medical images when the model training ends.

The first type of medical images may include a first type of image of a first body part, and the second type of medical images may include a second type of image of the first body part.

The first type of image may be an x-ray and the second type of image may be a CT scan.

The first body part may include chest or lung tissue.

The first type of medical images may include a first type of image of a first body part, and the second type of medical images may include a second type of image of a second body part.

The first body part may be one of a chest, femoral head and pulmonary tissue and the second body part may be one of a chest, cardiopulmonary tissue, and brain tissue.

The first and second type of images may be the same.

The raw data may include: coordinates data and pixel values, and the data attribute may include: a type of the coordinates data, a type of pixel values, and a dimension of medical images.

The step of performing the selected method of parameter transformation may include the steps of: reading the parameters of the model already trained, and constructing a parameter reading interface according to a format of the model already trained; establishing a pre-processing function for the parameters of the model already trained, wherein the step of establishing a pre-processing function includes intercepting, segmenting, mathematically transforming, mixing, changing order of the parameters; importing parameters of the model already trained after the completion of pre-processing into the model to be trained, and constructing a loading interface according to an input and output format of the model to be trained; and adjusting the parameter transformation according to corresponding analysis during the parameter transformation of the model to be trained.

When overall structures of the model to be trained and an overall structure of the model already trained have identical numbers of parameters and identical parameter structures, all of the parameters of the model already trained may be directly transferred to the model to be trained to start training.

The partial transfer method may include: when overall structures of the model to be trained and an overall structure of the model already trained are different, or if it is not desired to transfer all the parameters of the model already trained into the model to be trained, or if it is not desired that all the parameters of the model to be trained come from the model already trained, then some of the parameters in the model to be trained are transferred from the model already trained, while remaining parameters of the model to be trained are generated and adjusted in other methods.

The hybrid transfer method may include: combining the parameters of a plurality of models already trained simultaneously and transferring them into the model to be trained.

The parameter transform method may include: during the step of parameters transformation from the model already trained into the model to be trained, applying a mathematical transformation to the parameters of the model already trained, and then importing the parameters of the model already trained into the model to be trained.

The timing import method may include: during the step of parameters transformation from the model already trained into the model to be trained, the transformation is gradually performed during the training of the model to be trained according to the needs of the model to be trained.

The customized import method may include: during the step of parameters transformation from the model already trained into the model to be trained, the basic procedure, structure, objective, and methods of parameters transformation of the model already trained into parameters of the model to be trained are customized.

According to an exemplary embodiment, a device for performing transfer learning on medical images, include: a processer having a data processing module, a transformation learning module, and an application module; the data processing module being configured to read raw data information of a first type of medical images, to transform the raw data information by analyzing a data attribute of the raw data information, and to adjust the raw data into a data format of a model to be trained; the transformation learning module being configured to select a parameter transformation method by comparing parameters of the model to be trained with parameters of a model already trained, to perform the selected parameter transformation method, and to apply the transfer learning to the training of the model to be trained; the application module being configured to apply the parameters of the model already trained to the analysis for the first type of medical images when the model training ends; wherein the transformation methods of the transformation learning module include a complete transfer mode, a partial transfer mode, a hybrid transfer mode, a parameter transfer mode, a timing import method and a customized import method.

The processor may include: a parameter acquisition sub-module configured to read parameters of the model already trained, and to construct a parameter reading interface according to a format of the model already trained; a parameter pre-processing sub-module configured to perform pre-processing to the parameters of the model already trained, wherein the pre-processing includes intercepting, segmenting, mathematically transforming, mixing, and changing order of the parameters; a parameter import sub-module configured to import parameters of the model already trained after the completion of pre-processing into the model to be trained, and to construct a loading interface according to an input and output format of the model to be trained; and a model intervention sub-module configured to adjust the parameter transformation according to corresponding analysis during the training of the model to be trained.

The first type of medical images may be a first type of image of a first body part, and the second type of medical images may be a second type of image of the first body part.

The first type of medical images may be a first type of image of a first body part, and the second type of medical images may be a second type of image of a second body part.

The first and second type of images may be the same.

BRIEF DESCRIPTION OF THE DRAWINGS

The accompanying drawings, which are included to provide a further understanding of the invention and are incorporated in and constitute a part of this specification, illustrate exemplary embodiments of the invention, and together with the description serve to explain the inventive concepts.

DETAILED DESCRIPTION

Figure 1:
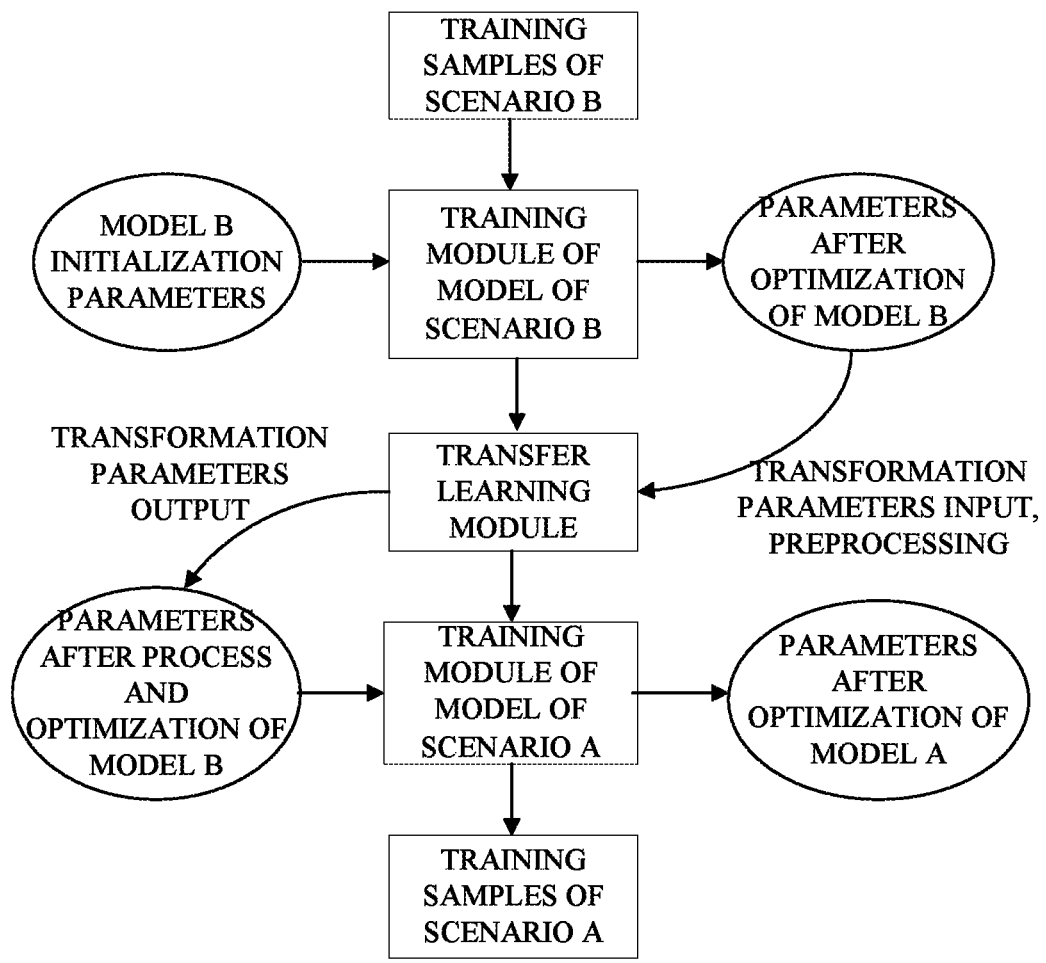
FIG. 1 is a schematic diagram of a method for performing transfer learning on medical images according to an exemplary embodiment of the invention.

In the following description, for the purposes of explanation, numerous specific details are set forth in order to provide a thorough understanding of various exemplary embodiments or implementations of the invention. As used herein "embodiments" and "implementations" are interchangeable words that are non-limiting examples of devices or methods employing one or more of the inventive concepts disclosed herein. It is apparent, however, that various exemplary embodiments may be practiced without these specific details or with one or more equivalent arrangements. In other instances, well-known structures and devices are shown in block diagram form in order to avoid unnecessarily obscuring various exemplary embodiments. Further, various exemplary embodiments may be different, but do not have to be exclusive. For example, specific shapes, configurations, and characteristics of an exemplary embodiment may be used or implemented in another exemplary embodiment without departing from the inventive concepts.

Unless otherwise specified, the illustrated exemplary embodiments are to be understood as providing exemplary features of varying detail of some ways in which the inventive concepts may be implemented in practice. Therefore, unless otherwise specified, the features, components, modules, layers, films, panels, regions, and/or aspects, etc. (hereinafter individually or collectively referred to as "elements"), of the various embodiments may be otherwise combined, separated, interchanged, and/or rearranged without departing from the inventive concepts.

The use of cross-hatching and/or shading in the accompanying drawings is generally provided to clarify boundaries between adjacent elements. As such, neither the presence nor the absence of cross-hatching or shading conveys or indicates any preference or requirement for particular materials, material properties, dimensions, proportions, commonalities between illustrated elements, and/or any other characteristic, attribute, property, etc., of the elements, unless specified. Further, in the accompanying drawings, the size and relative sizes of elements may be exaggerated for clarity and/or descriptive purposes. When an exemplary embodiment may be implemented differently, a specific process order may be performed differently from the described order. For example, two consecutively described processes may be performed substantially at the same time or performed in an order opposite to the described order. Also, like reference numerals denote like elements.

For the purposes of this disclosure, "at least one of X, Y, and Z" and "at least one selected from the group consisting of X, Y, and Z" may be construed as X only, Y only, Z only, or any combination of two or more of X, Y, and Z, such as, for instance, XYZ, XYY, YZ, and ZZ. As used herein, the term "and/or" includes any and all combinations of one or more of the associated listed items.

Although the terms "first," "second," etc. may be used herein to describe various types of elements, these elements should not be limited by these terms. These terms are used to distinguish one element from another element. Thus, a first element discussed below could be termed a second element without departing from the teachings of the disclosure.

The terminology used herein is for the purpose of describing particular embodiments and is not intended to be limiting. As used herein, the singular forms, "a," "an," and "the" are intended to include the plural forms as well, unless the context clearly indicates otherwise. Moreover, the terms "comprises," "comprising," "includes," and/or "including," when used in this specification, specify the presence of stated features, integers, steps, operations, elements, components, and/or groups thereof, but do not preclude the presence or addition of one or more other features, integers, steps, operations, elements, components, and/or groups thereof. It is also noted that, as used herein, the terms "substantially," "about," and other similar terms, are used as terms of approximation and not as terms of degree, and, as such, are utilized to account for inherent deviations in measured, calculated, and/or provided values that would be recognized by one of ordinary skill in the art.

As customary in the medical imaging and deep learning arts, some exemplary embodiments are described and illustrated in the accompanying drawings in terms of functional blocks, units, and/or modules. Those skilled in the art will appreciate that these blocks, units, and/or modules are physically implemented by electronic (or optical) circuits, such as logic circuits, discrete components, microprocessors, hard-wired circuits, memory elements, wiring connections, and the like, which may be formed using semiconductor-based fabrication techniques or other manufacturing technologies. In the case of the blocks, units, and/or modules being implemented by microprocessors or other similar hardware, they may be programmed and controlled using software (e.g., microcode) to perform various functions discussed herein and may optionally be driven by firmware and/or software. It is also contemplated that each block, unit, and/or module may be implemented by dedicated hardware, or as a combination of dedicated hardware to perform some functions and a processor (e.g., one or more programmed microprocessors and associated circuitry) to perform other functions. Also, each block, unit, and/or module of some exemplary embodiments may be physically separated into two or more interacting and discrete blocks, units, and/or modules without departing from the scope of the inventive concepts. Further, the blocks, units, and/or modules of some exemplary embodiments may be physically combined into more complex blocks, units, and/or modules without departing from the scope of the inventive concepts.

The invention provides a method for performing transfer learning on medical images, as shown in FIG. 1, which is a schematic diagram of a method of transfer learning according to an exemplary embodiment of the invention.

Scenario A is a desired medical scenario that could be learned and analyzed by deep learning, machine learning, or big data analysis. Scenario A could be medical images of pulmonary nodules, e.g. First, the training sample data related to scenario A are collected, and a training sample database is established. The model training module for scenario A is built on the basis of the training sample database, and the mathematical model used in the training module includes the basic framework (model layer) of the scenario A model and the parameters (parameter layer) of the framework. During the training process, the basic framework in the training module remains unchanged, but the parameters included in the basic framework are continuously updated, self-learned and optimized gradually round and round following the operation procedure, so that the model gradually possesses the expected analysis and intelligent effects.

When the model is very complex and the training samples are limited, the optimization process of scenario A is very difficult. In many cases, the model does not achieve the desired effect. The modeling and analysis process of scenario A would therefore easily fail. However, the parameter transfer learning method according to the principles of the invention effectively solves this problem. Scenario B is seen as another application scenario different from Scenario A, such as images of healthy pulmonary tissue or other body parts, but which has sufficient data and deep learning or big data model with very good results.

Therefore, the parameter transformation function required for the transfer learning is completed by performing parameter comparison between model A (to be analyzed) and model B (already trained). Using the parameter transfer learning method according to exemplary embodiments of the invention, the trained parameters in scenario B are obtained, processed and preprocessed, and transferred to the basic model framework of model A.

Therefore, model A establishes its parameter optimization procedure on the transformed parameters. It is unnecessary for the training module of model A to optimize the parameters from the beginning. On the contrary, it suffices to just optimize the parameters of model B. The parameters with strong feature mining ability in model B are effectively transformed into the model of application scenario A by a model parameter transfer learning method according to exemplary embodiments of the invention.

After the completion of parameter transformation, medical images are trained in the deep learning model. After the training, the parameters of model B are applied to the analysis of relevant medical images. This step includes applying the transfer learning to the deep learning model training of the particular medical image. When the model training ends, the parameters of model B may be applied to the analysis of categories of images.

For example, model A intends to train the deep learning model to analyze and achieve the characteristics of the pulmonary nodules on X-ray images, which assist diagnosis, but the model obtained by the analysis is less effective due to the limited amount of available data of pulmonary nodules. On the other hand, it is possible to have a large amount of X-ray data of pulmonary effusion and a well trained deep learning model B for pulmonary effusion. Therefore, the parameters of the X-ray model of pulmonary effusion obtained by training model B are input to model A for pulmonary nodules to start the deep learning. The training of model A greatly reduces the threshold of data volume because of its transformation by model B, thus the training results are greatly improved.

The X-ray data from pulmonary effusion could be used to train and develop the deep learning model of the field of X-ray data for pulmonary nodules due to the similarity exhibited by key components of the human body in a medical imaging scenario. The key components of the human body may include tissues, bones, and organs, which all exhibit different patterns from each other on a X-ray image, but also exhibit similar patterns over different parts of the body on a X-ray image. The similarity among the patterns of these key components may include the kinds of the color or the shade that represent them on X-ray image, or the type of certain concentration over a particular area of the image. According to other embodiments of the invention, it is possible to use even different body parts for training and developing the deep learning model than the desired body part.

Figure 2:
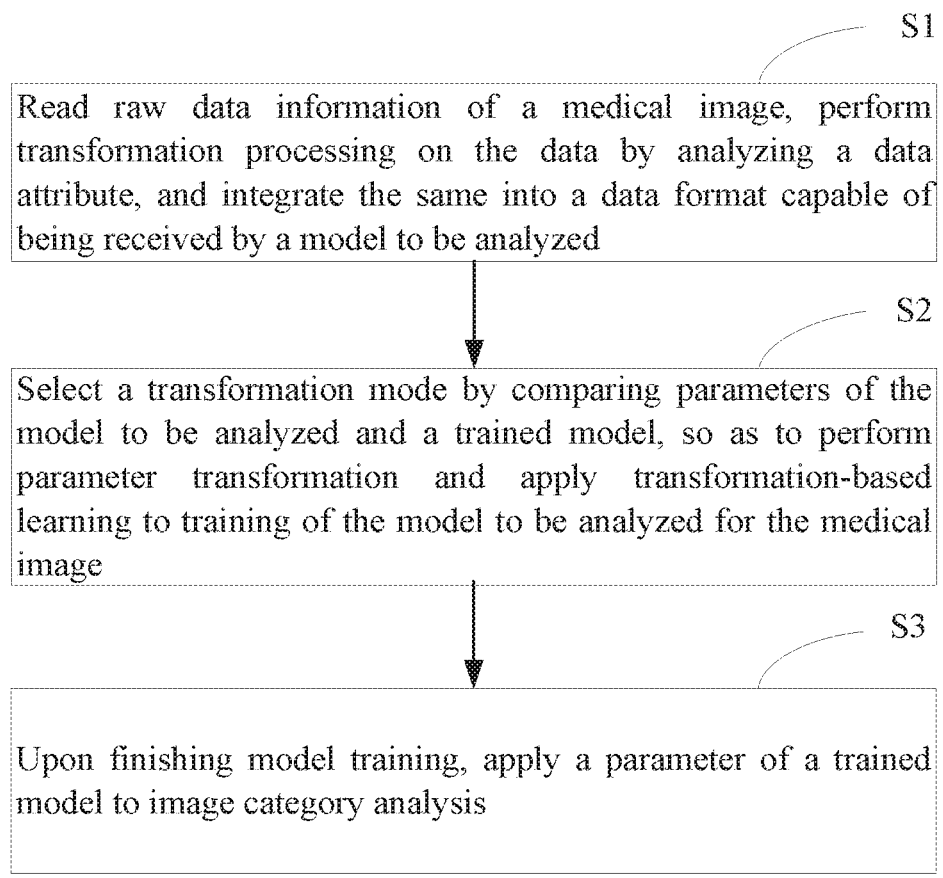
FIG. 2 is a flow chart of a method for performing transfer learning on medical images according to an exemplary embodiment of the invention.

As shown in FIG. 2, a method for transfer learning on medical images according to exemplary embodiment of the invention includes the steps of:

S1: reading raw data information related to a medical images, transforming the data by analyzing a data attribute, and adjusting the data into a data format that could be received by model A, as necessary, e.g. if the training data is two dimensional and the model data is three dimensional. The raw data may include coordinates data of certain patterns in the medical image, and the pixel values of the medical image. The data attribute may include the types of coordinates data of certain patterns in the medical image, the types of pixel values of the medical image, and the type of dimension of the image, such as whether the image is a three dimensional CT image or a two dimensional X-ray image. The transforming of the data may include adjusting the data format.

S2: selecting a transformation method by comparing parameters of model A and model B, thereby performing parameter transformation, and applying the transfer learning to the training of model A of medical images.

S3: applying parameters of model B to the analysis for the category of medical images when the model training ends. The parameters of model B may include the data that was transformed and changed data format in step S1.

The transformation methods of step 2 may include a complete transfer method, a partial transfer method, a hybrid transfer method, a parameter transformation method, a timing order import method and a customized import method, as is explained below in more detail.

Figure 3:
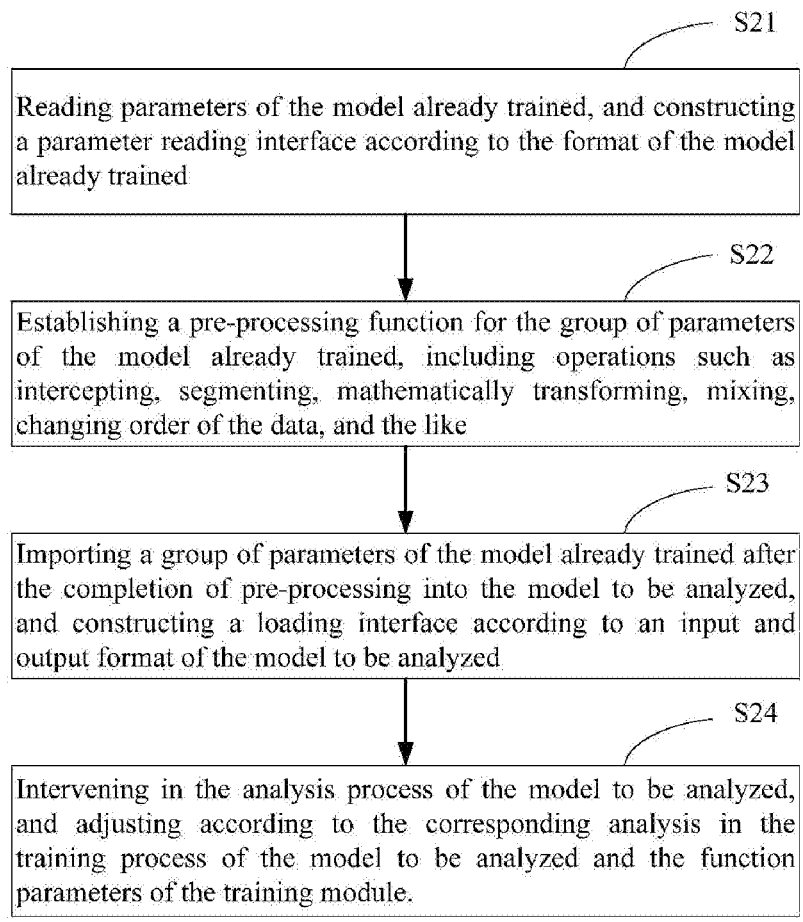
FIG. 3 is a flow chart of the parameter transformation steps of the method in FIG. 2.

As shown in FIG. 3, the parameter transformation in step S2 may include the steps of:

S21: reading the parameters of model B, and constructing a parameter reading interface according to the format of model B;

S22: establishing a pre-processing function for the group of parameters of model B, which includes operations such as intercepting, segmenting, mathematically transforming, mixing or changing order of the data, and the like;

S23: importing a group of parameters of model B after the completion of pre-processing into model A, and constructing a loading interface according to an input and output format of model A;

S24: intervening in the analysis process of model A, and adjusting according to is the corresponding analysis in the training process of model A and the function parameters of the training module.

During the process of model A training, intervention could be done to the training process of model A to adjust a series of control parameters during the training process of model A. For example, the parameter transformation module selectively adjusts the learning speed of various parameters of model A, lowers the learning speed of lower-level parameters, and assigns higher learning speed to higher-level model parameters, so that various parameters have different learning and adjustment speeds.

The transformation methods of parameters of model B into parameters of model A include a complete transfer method, a partial transfer method, a hybrid transfer method, a parameter transformation method, a timing import method and a customized import method, as is known in the art. The complete transfer method is when the overall structures of model A and model B are identical, having identical numbers of parameters and identical parameter structures, the parameters of model B are directly transferred as a whole to model A to start training; the partial transfer method is when the overall structures of model A and model B are different, or if it is not desired to transfer all the parameters of model B into model A, the parameter transformation module still transfers some of the parameters of model B into model A; or if it is not desired that all the parameters of model A come from model B, then some of the parameters in model A are transferred from model B, while the remaining parameters are generated and adjusted with other methods; the hybrid transfer method is when the parameters of the plurality of models (model B, model C, etc.) already trained are combined in a specific manner simultaneously and transferred into model A; the parameter transformation method is when, during the process of the parameter transformation module transforming parameters of model B into parameters of model A, the parameters of model B undergo a specific mathematical transformation, and then are imported into model A; the timing import method is when the process of the parameter transformation module transforming parameters of model B into parameters of model A, the transformation is gradually performed during the training process according to the requirements, instead of being completed at once; the customized import method is when the process of the parameter transformation module transforming parameters of model B into parameters of model A, the basic procedure, structure, objective, method and the like of the process of transforming parameters of model B into parameters of model A are customized, so that the process of parameter import is more suitable for actual application scenarios.

Figure 4:
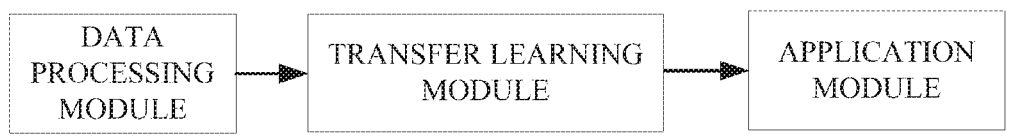
FIG. 4 is a block diagram of a portion of device for performing transfer learning on medical images constructed according to an exemplary embodiment of the invention.

As shown in FIG. 4, the invention also relates to a portion of a device for performing transfer learning on medical images, the device may include:

a data processing module that reads raw data information relating to medical images, transforms the data by analyzing data attributes, and adjusts the data into a data format that could be received by model A;

a transfer learning module that selects a transformation method by comparing parameters of model A and model B, thereby performs parameter transformation, and applies the transfer learning to the training of model A for medical images;

an application module that applies the parameters of model B to the analysis for the category of medical images when the model training ends.

Figure 5:
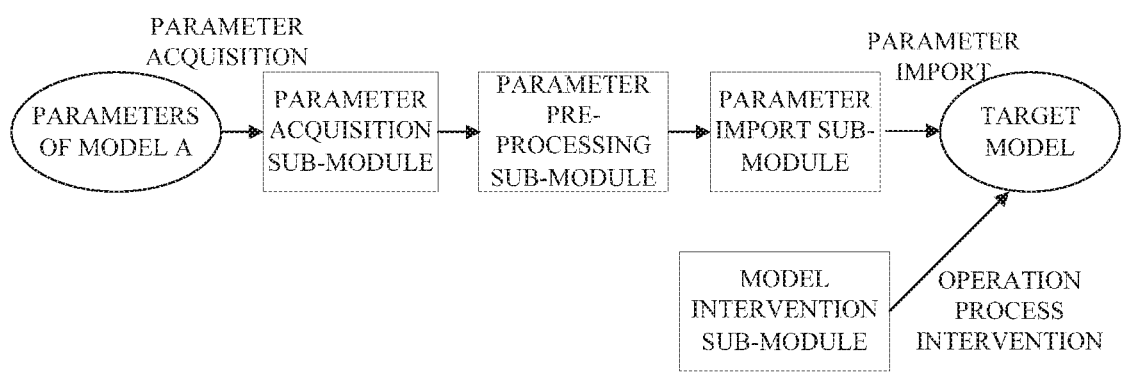
FIG. 5 is a block diagram of the transfer learning module in FIG. 3.

As shown in FIG. 5, it illustrates a block diagram of the transfer learning module of FIG. 4. The transfer learning module includes:

1) a parameter acquisition sub-module that reads parameters of model B, and is constructs a parameter reading interface according to the format of model B;

2) a parameter pre-processing sub-module that performs pre-processing to the group of parameters of model B, including operations such as intercepting, segmenting, mathematically transforming, mixing, changing order of the data, and the like;

3) a parameter import sub-module that imports a group of parameters of model B after the completion of pre-processing into model A, and constructs a loading interface according to an input and output format of model A; and 4) a model intervention sub-module that intervenes in the analysis process of model A, and adjusts according to the corresponding analysis in the training process of model A and the function parameters of the training module.

The following examples further illustrate how methods and devices constructed according to some exemplary embodiments of the invention operates.

First Example: perform transfer learning on the parameters of an intelligent analysis chest X-ray model so that the parameters apply to an intelligent analysis chest CT model.

It is assumed that a large amount of data has been learned and analyzed to have a dedicated chest X-ray model for analysis. Assuming that the data image dimension of each X-ray image is (1, 4096, 4096), the dimension list of the model parameter matrix used is: [32, 3, 3, 3], [64, 32, 3, 3], [128, 64, 3, 3], [2, 4096].

To analyze the chest CT model, assuming that the image dimension of each chest CT image is (300, 256, 256), and the model parameter list used is: [32, 300, 3, 3], [64, 32, 3, 3], [128, 64, 3, 3], [1000, 4096].

The chest X-ray model has sufficient amount of data and sufficient training, thus is the model is very effective. On the contrary, the targeted training chest CT model has insufficient amount of data and the model is huge and complex, therefore the training result is far from ideal. Therefore, a device for transfer learning of parameters of models constructed according to an exemplary embodiment of the invention is used, and includes: a data processing module that processes chest CT data into a format that is input into the chest CT model; and a transfer learning module that transforms the parameters of the chest X-ray model to train the chest CT model. The transfer learning module includes: parameter acquisition sub-module, a parameter pre-processing sub-module, a parameter import sub-module, a model intervention sub-module, and an application module.

The parameter acquisition sub-module obtains all parameter matrices from the parameters of the chest X-ray model and input them into the parameter acquisition sub-module.

The parameter pre-processing sub-module pre-processes the first layer parameter using a unique transformation method because the parameter dimension of the chest X-ray model is different from the parameter dimension of the chest CT model. This transformation makes use of the method that repeats the first layer parameter of the chest X-ray model 100 times on the second axis, with the last layer directly removed without any pre-processing as it is not loaded. The rest of the parameters are not pre-processed, and the transformation is directly performed on them, that is, the dimensions of the parameter matrices are transformed from [32, 3, 3, 3] to [32, 300, 3, 3], from [64, 32, 3, 3] to [64, 32, 3, 3], from [128, 64, 3, 3] to [128, 64, 3, 3].

The parameter import sub-module loads the parameters except the last layer of parameters of the chest X-ray model into the chest CT model and begins the training and analysis, thus the last layer of parameters in the chest CT model will not be transformed.

The model intervention sub-module intervenes the model training process after the chest CT model starts training and learning, performs slower updating and learning on the transformed first three layers of parameters, and performs higher learning and updating speeds on the last layer of parameters which is not transformed.

The application module would be operated after the chest CT model training is completed.

Second Example: perform transfer learning on the parameters of an intelligent analysis of the femoral head X-ray model so that the parameters apply to an intelligent analysis of cardiopulmonary X-ray model.

It is assumed that a large amount of data has been learned and analyzed with a dedicated femoral head model for analysis. Assuming that the data image dimension of each X-ray image is (1, 2000, 2000), the dimension list of the model parameter matrix used is: [32, 3, 3, 3], [64, 32, 3, 3], [128, 64, 3, 3], [2, 1024].

At this time, it is desired to analyze the cardiopulmonary X-ray model. Assuming that the image dimension of each cardiopulmonary X-ray image is (1, 2000, 2000), and the model parameter list used is: [32, 3, 3, 3], [64, 32, 3, 3], [128, 64, 3, 3], [2, 1024].

The femoral head X-ray model has sufficient amount of data and sufficient training, thus the model is very effective. On the contrary, the target training cardiopulmonary X-ray model has insufficient data amount therefore the training result is far from ideal. Therefore, a device for transfer learning of parameters of models constructed according to an exemplary embodiment of the invention is used, and the device includes: a data processing module, a transfer learning module, and an application module.

The data processing module processes cardiopulmonary X-ray data into a format that is input into the cardiopulmonary X-ray model;

The transfer learning module transforms the parameters of the femoral head X-ray model to train the cardiopulmonary X-ray model, the transfer learning module includes: a parameter acquisition sub-module, a parameter pre-processing sub-module, a parameter import sub-module, a model intervention sub-module.

The parameter acquisition sub-module obtains all parameter matrices from the parameters of the femoral head X-ray model and input them into the parameter acquisition sub-module;

The parameter pre-processing sub-module, wherein the transformation adopts the parameter complete transformation method because the parameter dimensions of the femoral head X-ray model are identical to the parameter dimensions of the cardiopulmonary X-ray model.

The parameter import sub-module loads the parameters of the femoral head X-ray model into the cardiopulmonary X-ray model, but the parameters being loaded might not include the last layer of the parameters, then the parameter import sub-module begins the training and analysis, thus the last layer of parameters in the cardiopulmonary X-ray model will not be transformed.

The model intervention sub-module that intervenes the model training process after the cardiopulmonary X-ray model starts training and learning, performs slower updating and learning on the transformed first three layers of parameters, and assigns higher learning and updating speeds to the last layer of parameters which are not transformed.

The application module would be operated after the cardiopulmonary X-ray model training is completed.

Third Example: perform transfer learning on the parameters of an intelligent analysis of pulmonary CT model so that the parameters apply to an intelligent analysis of brain MRI model.

It is assumed that a large amount of data has been learned and analyzed with a dedicated pulmonary CT model for analysis. Assuming that the dimension of the data image being input into the CT model is (1,100, 512, 512), the dimension list of the model parameter matrix used is: [32, 100, 3, 3], [64, 32, 3, 3], [128, 64, 3, 3], [1, 1024].

At this time, it is desired to analyze the brain Mill model. Assuming that the image dimension of each slice of brain Mill image is (1,100, 256, 256), and the model parameter list used is: [32, 100, 3, 3], [64, 32, 3, 3], [128, 64, 3, 3], [256, 128, 3, 3], [1, 1024].

The pulmonary CT model has sufficient amount of data and sufficient training, thus the model is very effective. On the contrary, the target training brain MRI model has insufficient amount of data, therefore the training result is far from ideal. Therefore, a device for transfer learning of parameters of models constructed according to an exemplary embodiment of the invention is used, and includes: a data processing module, a transfer learning module, and an application module.

The data processing module processes brain Mill data into a format that is input into the brain MRI model;

The transfer learning module transforms the parameters of the pulmonary CT model to train the brain MM model, that the transfer learning module includes: a parameter acquisition sub-module, a parameter pre-processing sub-module, a parameter import sub-module, and a model intervention sub-module.

The parameter acquisition sub-module obtains all parameter matrices from the parameters of the pulmonary CT model and input them into the parameter acquisition sub-module;

The parameter pre-processing sub-module, wherein the transformation uses the parameter partial transformation method because that although the parameter dimensions of the pulmonary CT model are identical to the parameter dimensions of the brain Mill model, the number of parameters are different.

The parameter import sub-module loads the parameters of parameters of the pulmonary CT model except the last layer into the brain MM model, while the extra set of parameters [256, 128, 3, 3] of the brain Mill model adopts an initialization of random numbers following Gaussian distribution, then the training and analysis begins.

The model intervention sub-module intervenes the model training process after the brain MRI model starts training and learning, performs slower updating and learning on the transformed first three layers of parameters, and performs higher learning and updating speeds to the last layer of parameters which are not transformed.

The application module would be operated after the brain MRI model training is completed.

Figure 6:
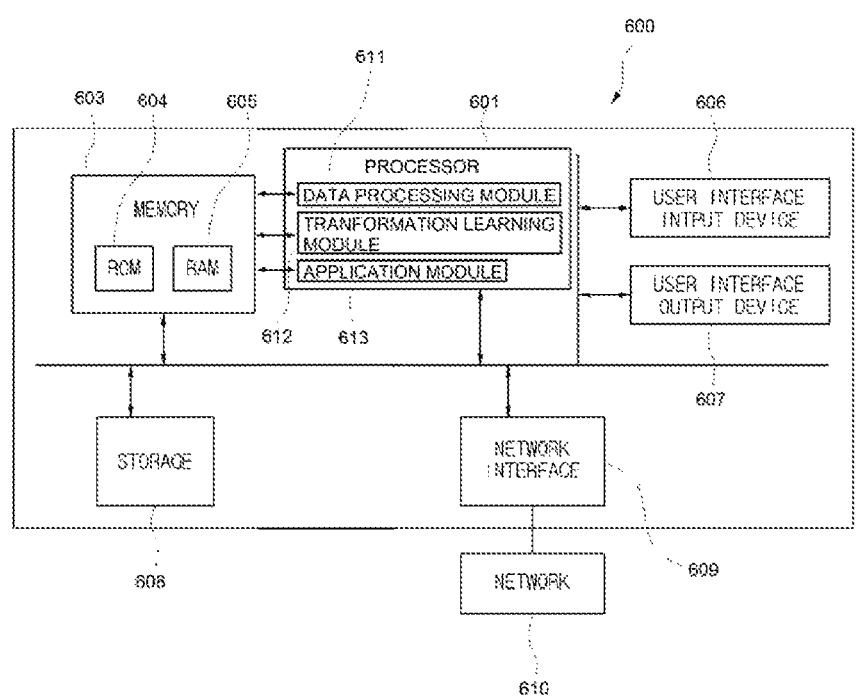
FIG. 6 is block diagram of a system for performing the transfer learning on medical images according to an exemplary embodiment of the invention.

In FIG. 6, an embodiment of the invention may be implemented in a computer system, e.g., as a computer readable medium. As shown in in FIG. 6, a computer system 600 may include one or more of a processor 601, a memory 603, a user input device 606, a user output device 807, and a storage 608, each of which communicates through a bus 602. The computer system 600 may also include a network interface 609 that is coupled to a network 610. The processor 601 may be a GPU, a CPU, or a semiconductor device that executes processing instructions stored in the memory 603 and/or the storage 608. The processor 601 may include a data processing module 611, a transformation learning module 612, and an application module 613, and each of the modules may transfer data to or/and from the memory 603 during the transformation learning process. The processor 601 as a whole may also interact with the network interface 609, the network 610, the user interface input device 608, and the use interface output device 607. The data processing module 611, the transformation learning module 612, and the application module 613 are the same as described above in FIG. 4, thus a detailed description will be omitted. The memory 603 and the storage 608 may include various forms of volatile or non-volatile storage media. For example, the memory may include a read-only memory (ROM) 604 and a random access memory (RAM) 605.

Accordingly, an embodiment of the invention may be implemented as a computer implemented method or as a non-transitory computer readable medium with computer executable instructions stored thereon. In an embodiment, when executed by the processor, the computer readable instructions may perform a method according to at least one aspect of the invention.

Although certain exemplary embodiments and implementations have been described herein, other embodiments and modifications will be apparent from this description. Accordingly, the inventive concepts are not limited to such embodiments, but rather to the broader scope of the appended claims and various obvious modifications and equivalent arrangements as would be apparent to a person of ordinary skill in the art.

What is claimed is:

1. A method for performing transfer learning on medical images, comprising the steps of:
reading raw data related to a first type of medical images, transforming the raw data by analyzing a data attribute of the raw data, and adjusting the raw data into a data format of a model to be trained for a second type of medical images;
selecting a parameter transformation method from the group consisting of a complete transfer method, a partial transfer method, a hybrid transfer method, a parameter transformation method, a timing import method, and a customized import method by comparing parameters of the model to be trained with parameters of a model already trained;
performing the selected method of parameter transformation, and applying the transfer learning to training of the model for the first type of medical images; and
applying the parameters of the model already trained to the analysis for the second type of medical images when the model training ends,
wherein the performing the selected method of parameter transformation further comprises the steps of:
reading the parameters of the model already trained, and constructing a parameter reading interface according to a format of the model already trained;
establishing a pre-processing function for the parameters of the model already trained, wherein the step of establishing a pre-processing function includes intercepting, segmenting, mathematically transforming, mixing, changing order of the parameters;
importing parameters of the model already trained after the completion of pre-processing into the model to be trained, and constructing a loading interface according to an input and output format of the model to be trained; and
adjusting the parameter transformation according to corresponding analysis during the parameter transformation of the model to be trained.

2. The method of claim 1, wherein the raw data further comprises: coordinates data and pixel values, and the data attribute further comprises: a type of the coordinates data, a type of pixel values, and a dimension of medical images.

3. The method of claim 1, wherein the complete transfer method comprises:
when overall structures of the model to be trained and an overall structure of the model already trained have identical numbers of parameters and identical parameter structures, all of the parameters of the model already trained are directly transferred to the model to be trained to start training.

4. The method of claim 1, wherein the partial transfer method comprises:
when overall structures of the model to be trained and an overall structure of the model already trained are different, or if it is not desired to transfer all the parameters of the model already trained into the model to be trained, or if it is not desired that all the parameters of the model to be trained come from the model already trained, then some of the parameters in the model to be trained are transferred from the model already trained, while remaining parameters of the model to be trained are generated and adjusted in other methods.

5. The method of claim 1, wherein the hybrid transfer method comprises:
combining the parameters of a plurality of models already trained simultaneously and transferring them into the model to be trained.

6. The method of claim 1, wherein the parameter transform method comprises that:
during the step of parameters transformation from the model already trained into the model to be trained, applying a mathematical transformation to the parameters of the model already trained, and then importing the parameters of the model already trained into the model to be trained.

7. The method of claim 1, wherein the timing import method comprises:
during the step of parameters transformation from the model already trained into the model to be trained, the transformation is gradually performed during the training of the model to be trained according to the needs of the model to be trained.

8. The method of claim 1, wherein the customized import method comprises:
during the step of parameters transformation from the model already trained into the model to be trained, the basic procedure, structure, objective, and methods of parameters transformation of the model already trained into parameters of the model to be trained are customized.

9. A device for performing transfer learning on medical images, comprising:
- a processor having a data processing module, a transformation learning module, and an application module;
- the data processing module being configured to read raw data of a first type of medical images, to transform the raw data by analyzing a data attribute of the raw data, and to adjust the raw data into a data format of a model to be trained;
- the transformation learning module being configured to select a parameter transformation method by comparing parameters of the model to be trained with parameters of a model already trained, to perform the selected parameter transformation method, and to apply the transfer learning to the training of the model to be trained;
- the application module being configured to apply the parameters of the model already trained to the analysis for the first type of medical images when the model training ends;
- wherein the transformation methods of the transformation learning module include a complete transfer mode, a partial transfer mode, a hybrid transfer mode, a parameter transfer mode, a timing import method and a customized import method,
- wherein the processor further comprises:
  - a parameter acquisition sub-module configured to read parameters of the model already trained, and to construct a parameter reading interface according to a format of the model already trained;
  - a parameter pre-processing sub-module configured to perform pre-processing to the parameters of the model already trained, wherein the pre-processing includes intercepting, segmenting, mathematically transforming, mixing, and changing order of the parameters;
  - a parameter import sub-module configured to import parameters of the model already trained after the completion of pre-processing into the model to be trained, and to construct a loading interface according to an input and output format of the model to be trained; and,
  - a model intervention sub-module configured to adjust the parameter transformation according to corresponding analysis during the training of the model to be trained.

10. The device of claim 9, wherein the first type of medical images comprises a first type of image of a first body part, and the second type of medical images comprises a second type of image of the first body part.

11. The device of claim 9, wherein the first type of medical images comprises a first type of image of a first body part, and the second type of medical images comprises a second type of image of a second body part.

12. The device of claim 9, wherein the first and second type of images are the same.

* * * * *